(12) United States Patent
Lijoi

(10) Patent No.: US 11,497,578 B2
(45) Date of Patent: Nov. 15, 2022

(54) SUPPORT FOR MEDICAL INSTRUMENTS

(71) Applicant: Giuseppe Lijoi, Marino (IT)

(72) Inventor: Giuseppe Lijoi, Marino (IT)

( * ) Notice: Subject to any disclaimer, the term of this patent is extended or adjusted under 35 U.S.C. 154(b) by 373 days.

(21) Appl. No.: 16/635,889

(22) PCT Filed: Aug. 1, 2018

(86) PCT No.: PCT/IT2018/050144
§ 371 (c)(1),
(2) Date: Jan. 31, 2020

(87) PCT Pub. No.: WO2014/030785
PCT Pub. Date: Feb. 14, 2019

(65) Prior Publication Data
US 2021/0052350 A1    Feb. 25, 2021

(30) Foreign Application Priority Data

Aug. 4, 2017   (IT) .......................... 10201700090466

(51) Int. Cl.
*F16M 11/00* (2006.01)
*A61B 90/53* (2016.01)
*A61B 1/00* (2006.01)
*F16M 13/02* (2006.01)
*F16M 13/04* (2006.01)

(52) U.S. Cl.
CPC .......... *A61B 90/53* (2016.02); *A61B 1/00149* (2013.01); *F16M 13/022* (2013.01); *F16M 13/04* (2013.01); *F16M 2200/022* (2013.01); *F16M 2200/06* (2013.01)

(58) Field of Classification Search
CPC .. A61B 90/53; A61B 1/00149; F16M 13/022; F16M 13/04
See application file for complete search history.

(56) References Cited

U.S. PATENT DOCUMENTS

| 4,158,490 A * | 6/1979 | Gottschalk ......... F16M 11/2092 |
| | | 396/420 |
| 9,335,112 B1* | 5/2016 | Sholley ................ F41C 33/001 |
| 10,512,322 B2* | 12/2019 | Washington ......... F16M 13/022 |
| 2006/0106280 A1* | 5/2006 | Surti .................. A61B 1/00147 |
| | | 600/102 |
| 2012/0197075 A1 | 8/2012 | Krimsky et al. |
| 2013/0004153 A1* | 1/2013 | McKee ................. F16M 11/14 |
| | | 396/419 |

(Continued)

OTHER PUBLICATIONS

International Search Report and Written Opinion of PCT/IT2018/050144 dated Nov. 30, 2018, 10 pages.
Search Report of IT 10201700090466 dated Apr. 11, 2018, 2 pages.

*Primary Examiner* — Amy J. Sterling
(74) *Attorney, Agent, or Firm* — Rankin, Hill & Clark LLP

(57) ABSTRACT

The medical instrument support device comprises a harness with a plate (1) which can be fixed by means of straps, a fastening element (3) and a second fastening element (4) which can be attached to and is detachable from the first fastening element (3), an articulated joint (5) of tubular and elongated shape, fixed integrally and removable at its end to the first fixing element (3) and supporting at its second end a housing (6) angularly adjustable in space and fixable in any position angular with a manual clamp (7), where the housing (6) is configured to support the medical device.

12 Claims, 6 Drawing Sheets

(56) References Cited

U.S. PATENT DOCUMENTS

| | | | | |
|---|---|---|---|---|
| 2013/0048818 A1* | 2/2013 | Von Pechmann | F16M 11/40 | |
| | | | | 248/276.1 |
| 2013/0214022 A1* | 8/2013 | Harvey | F16M 11/041 | |
| | | | | 224/623 |
| 2014/0161433 A1* | 6/2014 | Steinhauser | F16M 11/14 | |
| | | | | 396/420 |
| 2014/0231482 A1* | 8/2014 | Chamberlayne | F16M 13/04 | |
| | | | | 224/623 |
| 2014/0339382 A1* | 11/2014 | Steubing | F16M 11/2028 | |
| | | | | 248/128 |
| 2017/0119132 A1* | 5/2017 | Pruess | F16M 11/32 | |
| 2017/0269459 A1* | 9/2017 | Tipson | F16M 13/00 | |
| 2021/0255450 A1* | 8/2021 | Ackerman | G02B 23/18 | |
| 2022/0074543 A1* | 3/2022 | Barilotti | H04M 1/05 | |

* cited by examiner

SUPPORT FOR MEDICAL INSTRUMENTS

FIELD OF INVENTION

The present invention relates to a device to be attached to the body of an operator to support medical and surgical instruments, in particular to a harness to support endoscopes and optical devices for endoscopies and laparoscopies.

STATE OF THE ART

When an operator, a doctor or a health professional has to perform operations or examinations on a patient's body, he must use tools such as endoscopes or similar devices and sometimes these devices are of such a size that it is difficult for a single operator to support and operate them alone at the same time, therefore the intervention of a second operator is required to support the first one. It is known from US20120197075 a support device for medical instruments that has insufficient versatility in arranging medical instruments and is cumbersome for the operator who wears it. It is felt the need to have support devices that are easy to use and that make the way of operating with medical or surgical instruments to medical or paramedical staff easier and lighter and more autonomous.

SUMMARY OF THE INVENTION

In order to solve these problems, the invention provides a support device with the features of claim 1. Thanks to its peculiar characteristics, the device of the invention allows to facilitate all the procedures performed by using flexible endoscopes and instruments which use optical devices by having the possibility of relieving the joints of the upper limbs of the operator from the weight of the instrument and any camera mounted on the latter and at the same time giving the possibility to have the instrument positioned in any desired position and then keep said position. At the same time the support device of the invention allows the operator to have his hands free from the instrument in order to perform other actions performed otherwise by a second operator. Another important advantage of the support device of the invention is to avoid inconvenient positions during the whole course of the examination and the functional overload of the joints of the upper limbs of the operator. It allows to perform a medical examination in a more autonomous, fast and desired way because there is the possibility, when necessary, to have the hands free from the instrument leaving it fixed in the desired position.

In one of the advantageous embodiments of the invention, the presence of the frictional multi-spherical joint allows an unlimited spatial positioning and therefore it allows to perform, reproduce and support any movement that the operator makes and to leave the operating instrument, e.g. a flexible endoscope, but not exclusively, fixed in virtually any desired position leaving the operator's hands free without the tool changing position. In this way the operator can perform those actions that otherwise would have to be performed with a support operator, extending the execution time and increasing costs.

Another advantage of the device of the invention is that it can be disassembled thanks to a guided engagement system which allows to release the multi-spherical articulated joint from the plate which remains attached to the operator through the sling. This exclusive feature for this type of device allows the device to be used also in procedures involving a sterile operating field, leaving the plate of the support device (not sterile) attached to the operator who then wears the sterile gown and connecting the articulated (sterile) joint through the guided grafting system that provides for the overlap of the fabric of the sterile gown.

The characteristic of being demountable also has the advantage of simplifying the procedures of sterilization/sanitization of the device which provides for a sterilization procedure only for the articulated multi-spherical joint and for sanitizing the plate, reducing costs.

Furthermore, the compactness of the quick coupling allows the operator wearing the device to have a small encumbrance in front of the chest, allowing him greater freedom of movement and greater closeness to the patient when this is necessary.

Further advantages are the possibility of interchanging the joints so as to make the device more suitable for the various uses and the possibility of interchanging the housing present at the end of each joint to accommodate the various types of instruments used in the examinations.

The multi-spherical articulated joint and the housings at the end of the multi-spherical articulated joint are foreseen in all its variants also in disposable material to reduce completely the costs of sterilization.

BRIEF DESCRIPTION OF THE FIGURES

Further characteristics and advantages of the invention will become clearer in the light of a detailed description of a preferred but not exclusive embodiment of a support device according to the invention, illustrated by way of non-limiting example, with the aid of the accompanying figures in which.

DETAILED DESCRIPTION OF PREFERRED EMBODIMENTS OF THE INVENTION

Figure 1:
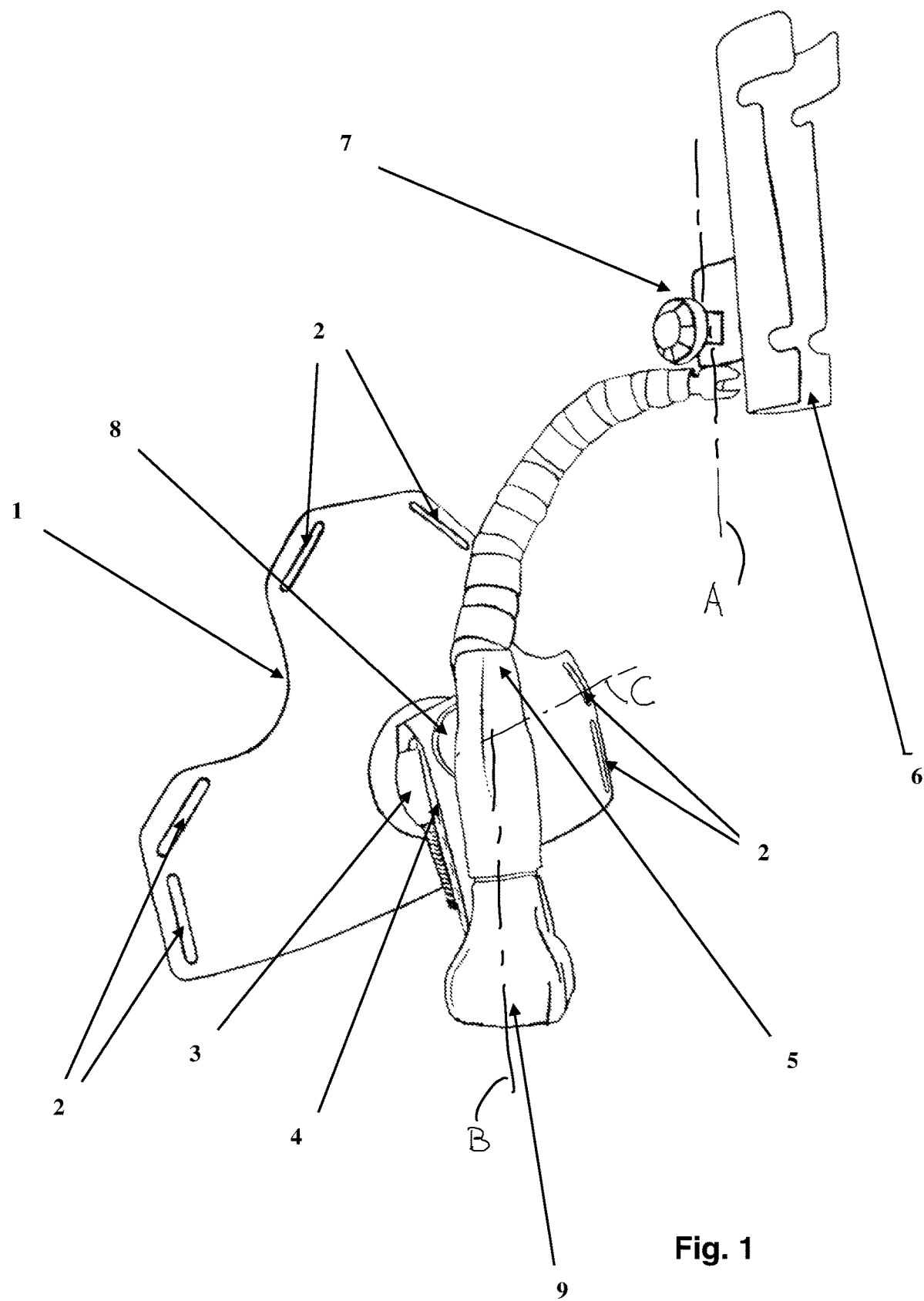
FIG. 1 and FIG. 2 represent an overall view of the device of the invention.

The support provides a harness which comprises the plate 1 made of light material, advantageously rigid, of an approximate but not necessarily triangular shape and shaped so as to position itself appropriately on the chest or abdomen of an operator, it is provided with slots 2 for inserting belts or equivalent means to secure the plate 1 securely to the torso; when worn by the operator the plate is intended to be positioned substantially vertically or at least parallel to the operator's chest.

On the plate 1 a special support 3 is fastened with a quick guided coupling for a complementary element 4 so as to create a snap coupling or another attachment which can be attached and detachable in a simple and rapid manner of constitution similar to that of a known type of snap with an elastic expandable element which is pressed onto the support and is removed by pulling it with a force which makes the elastic element detach from the support.

In another variant the quick coupling can be made with a gripper element in the complementary element 4 which tightens the support 3 protruding from the plate, with a lever which opens and closes the gripper, which can be controlled by the hand of the operator. The quick coupling allows a fastening on the plate of the complementary element 4 also through a gown or another protective cover of the operator so as to prevent contact with the plate of the harness to avoid contamination, or that the operator gets infected, in case he operates near to a contagious patient.

The complementary element 4 is connected to a frictional multi-spherical articulated joint 5. The multi-spherical articulated joint 5 is made up of segments in the form of spheres and alternating with segments of cylindrical shape with two cavities in the form of spherical caps complementary to the sphere-shaped segments and all are joined to each other so as to form a chain succession held together by a cable inside the articulated joint under tension which holds the sphere-shaped and cylinder-shaped segments in mutual frictional contact. In this way, the segments are maintained in mutual position by means of the friction existing between two segments. The position between the segments can be changed by applying a force sufficient to overcome the frictional forces between the segments.

The articulation has a knob 9 to regulate the internal cable tension in order to adjust the friction force. This knob is rotating around an axis B, and can be operated by the operator, which allows the multi-spherical joint 5 to be tightened, increasing the tension of the cable arranged inside to fix it in a certain position and the loosening of the multi-spherical joint 5 to change its shape. The multi-spherical articulated joint 5 is interchangeable with other joints based on the type of diagnostic test to be performed.

An interchangeable housing 6 with a shape and conformation connection adapted to support the medical instrument, for example an endoscope, not shown, is fixed at the end of the articulated joint 5 opposite to the one connected to the complementary element 4. The shape of the housing 6 is chosen based on the instrument used and the type of diagnostic test to be performed.

Figure 2:
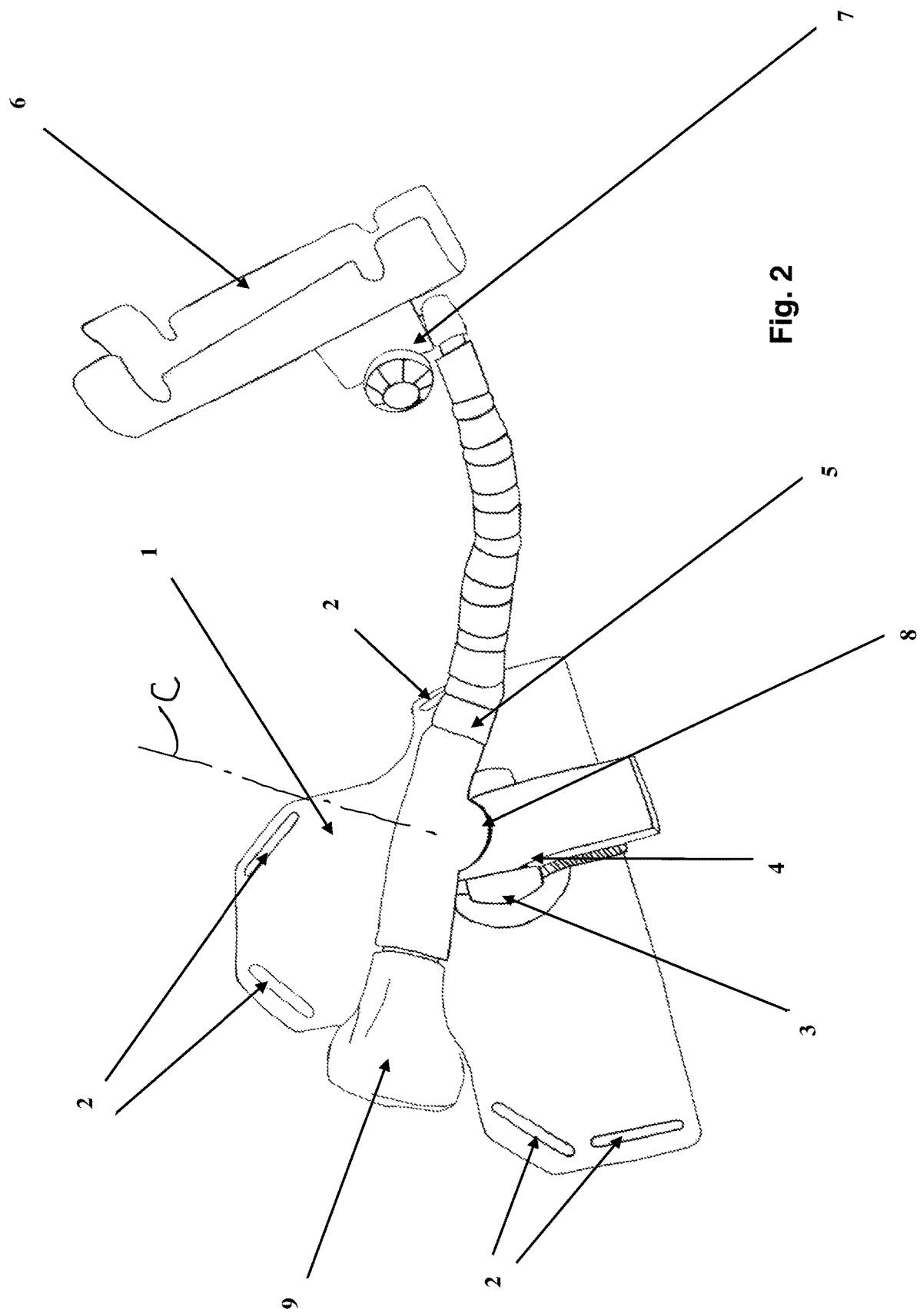
Figure 3:
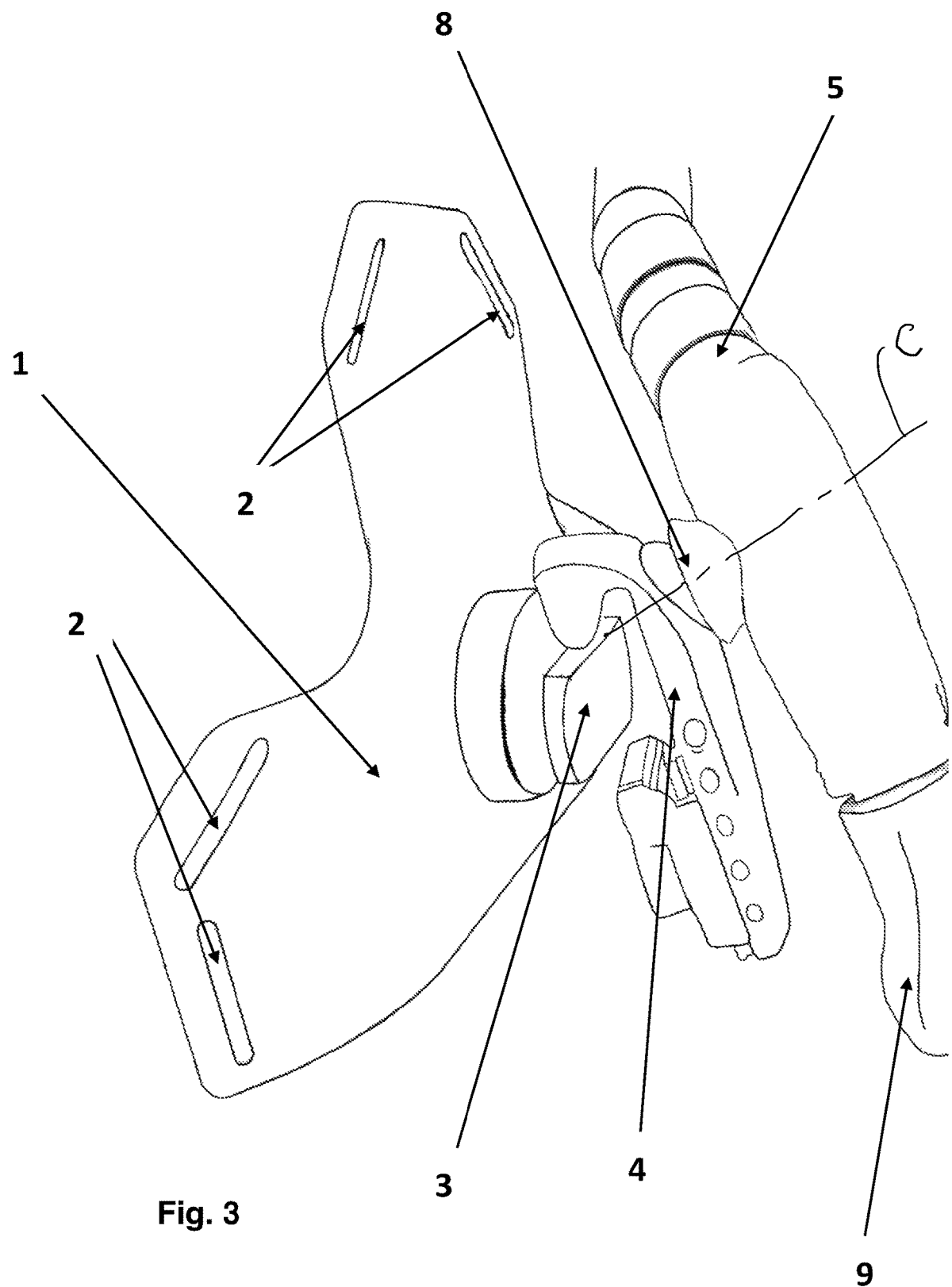
FIG. 3 shows an enlarged axonometric view of a first detail of FIGS. 1 and 2.
Figure 4:
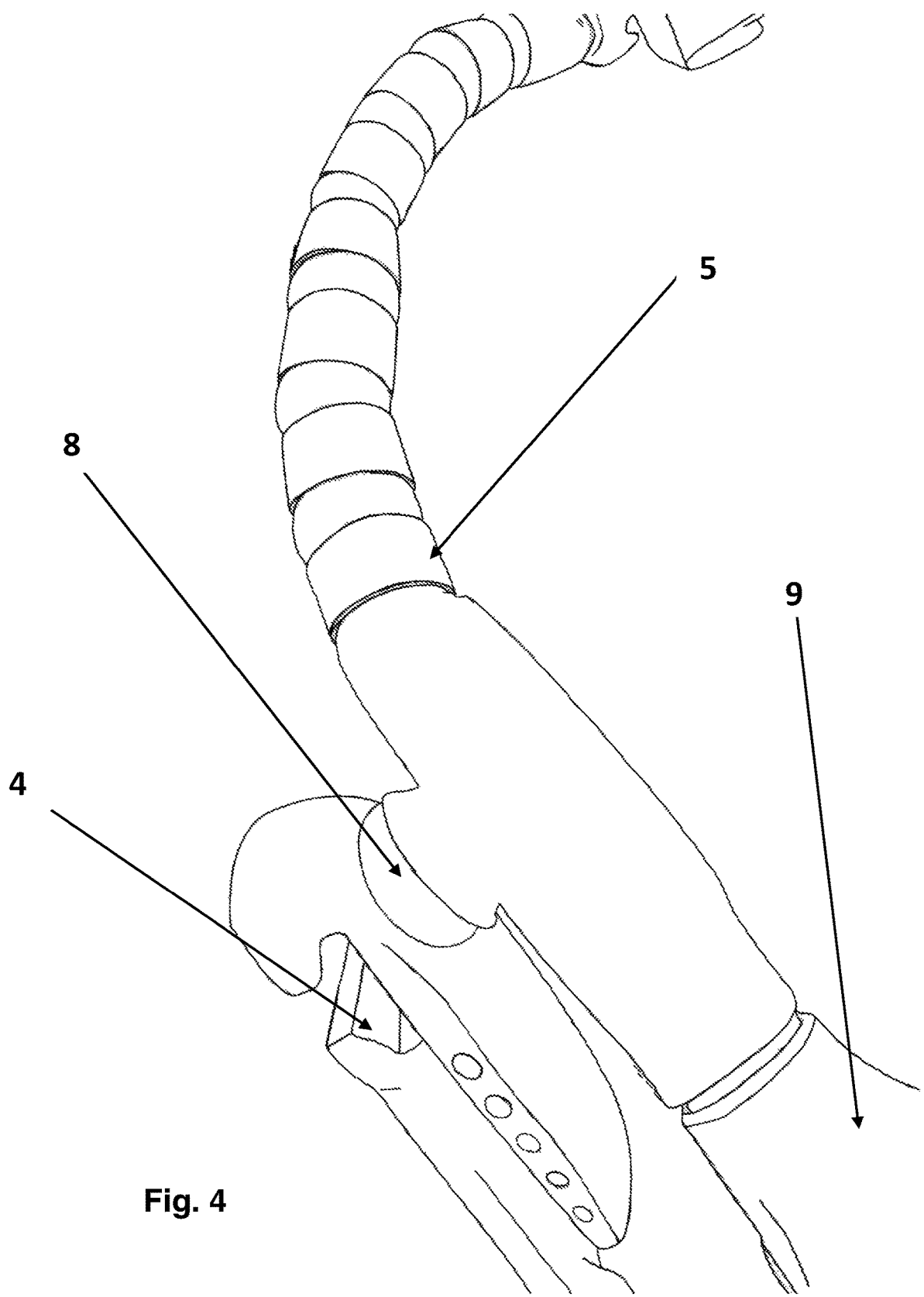
FIG. 4 shows an enlarged axonometric view of a second detail of FIGS. 1 and 2.
Figure 5:
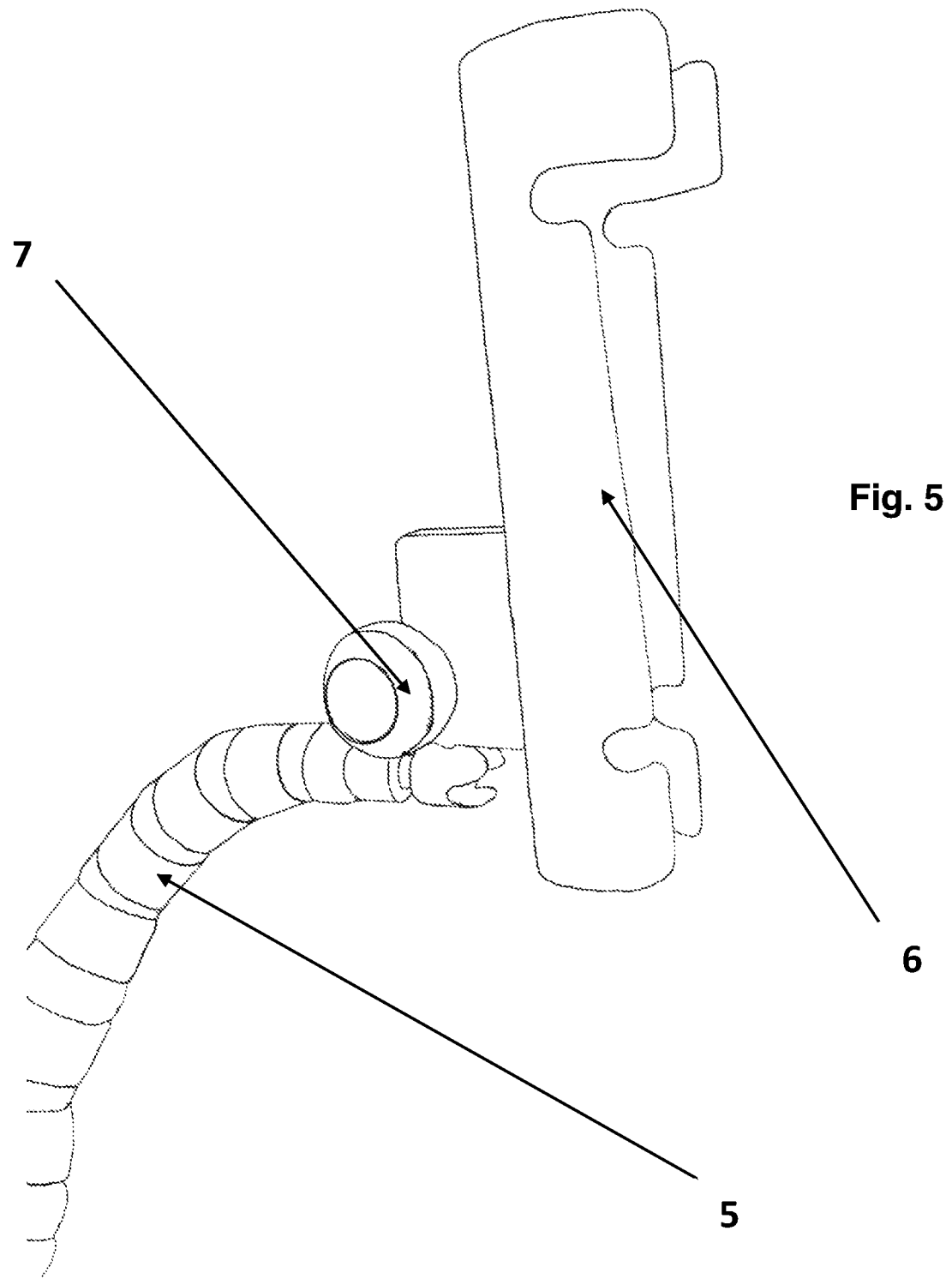
FIG. 5 shows an enlarged axonometric view of a third detail of FIGS. 1 and 2.
Figure 6:
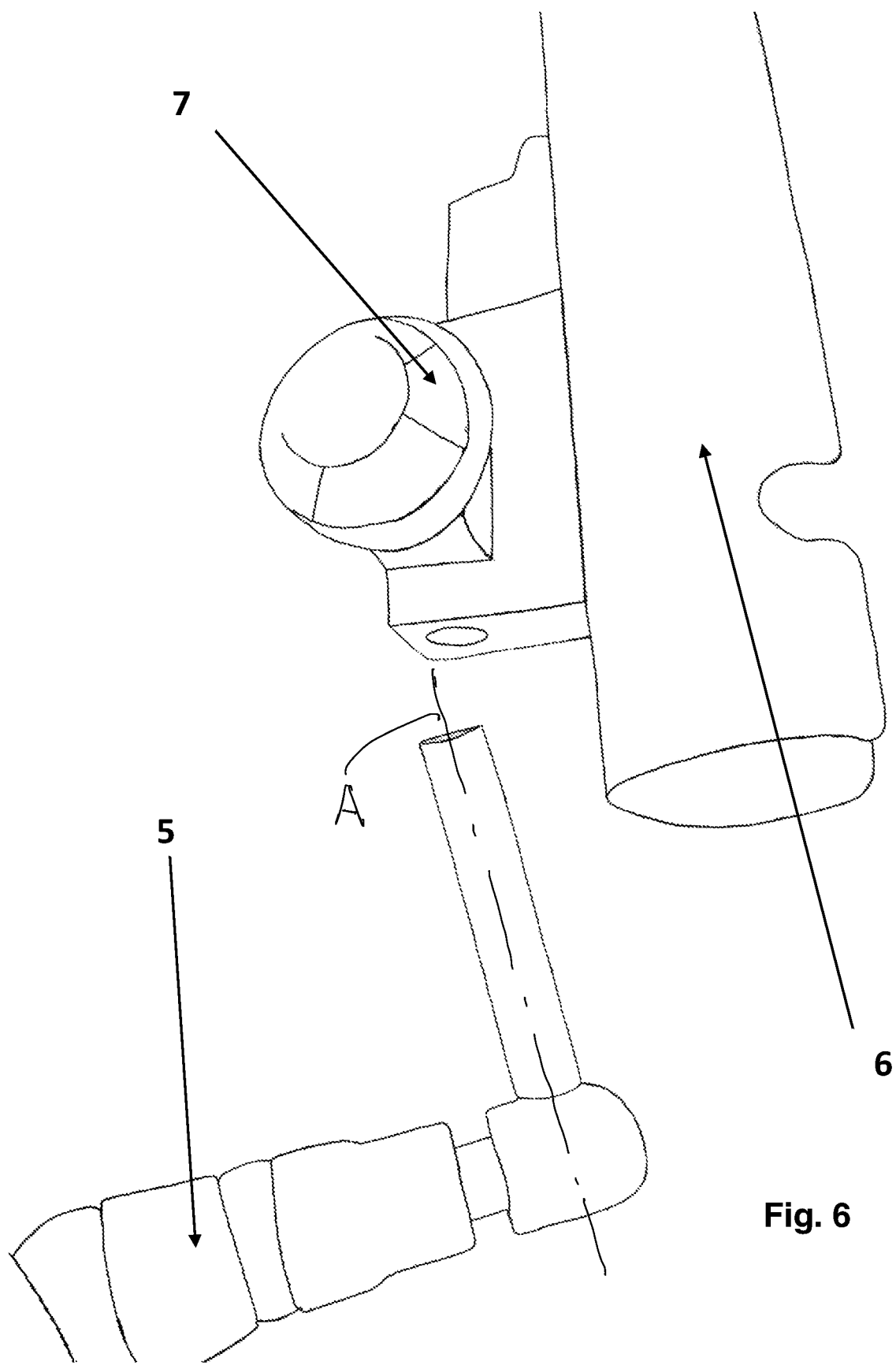
FIG. 6 shows an enlarged axonometric view of a third detail of FIGS. 1 and 2.

The multi-spherical articulated joint 5 has an adjustable flexibility so as to allow a positioning in the space of the housing 6. The interchangeable housing 6 provides for its autonomous mobility independently of the multi-spherical articulated joint 5. A lockable articulated joint 7 is also provided which rotates around an axis A allowing the housing 6 a further spatial positioning in any angular position about the axis A for an arc of almost 360 degrees and with a screw which allows fixing it in the position desired by the operator and that can also be adjusted in its rigidity until complete blocking of the same through the lockable joint 7. Moreover, the complementary fastening element 4, as shown in FIG. 2, can rotate throughout the azimuth around an axis C substantially perpendicular to the plate 1, preferably at an angle with respect to the line perpendicular to the bottom plate that is less than 30°, adding in this way a further element of flexibility.

The support device of the invention as described above facilitates the operator during the examination, leaving his hands free to carry out those operations that otherwise would have been subordinated to the presence of a second operator who in fact slows down the whole executive process for the times that elapse from giving the command (from the operator) to its execution (by the help) and that is not always simultaneous and therefore can be repeated until the achievement of the expected result. Furthermore, there is the advantage of relieving the joints of the upper limbs of the operator from the weight of the endoscope and of a possible accessory external camera. This is due to the distribution of the entire weight on the harness plate that distributes it to the muscles of the torso, the hips and the legs.

The invention has been described so far with specific reference to some preferred embodiments. However, it is possible to make changes within the scope of protection of the invention described in the foregoing and defined by the appended claims.

The invention claimed is:

1. Medical instrument support device comprising a harness with a plate that is fixable by means of straps on the chest of an operator, a first fastening element projecting directly from the plate in a direction perpendicular to the chest and a second complementary fastening element that is attachable to and detachable from the first fastening element, said second complementary element being able to rotate about an axis substantially perpendicular to said plate, an articulation element having a tubular and elongated shape and a first and a second end, in which it is fixed integrally and removably at its first end to the second complementary fastening element and supporting at its second end a housing angularly adjustable in space and which is fixable in any angular position around a substantially vertical axis by means of a clamp, the housing being configured to support an associated medical instrument and the articulation element being flexible so as to allow its deformation to assume a sinuous shape for a positioning of the housing in space.

2. Device according to claim 1, wherein the articulation element consists of segments joined to each other so as to form a chain succession and each segment is held in friction contact to the adjacent segments by means of a tension element so as to maintain a mutual position by means of friction.

3. Device according to claim 2, wherein adjustment means of the tension element are provided for regulating the friction force.

4. Device according to claim 3, wherein the second complementary fastening element is snap fastened to the first fastening element exerting pressure or tension respectively for extraction or insertion.

5. Device according to claim 3, wherein the second complementary fastening element is fastened to the first fastening element by means of a gripper which tightens the first fastening element and that is operable in closed or open position by means of a lever control, in such a way that said second element is rotatable throughout the azimuth around said axis perpendicular to the plate.

6. Device according to claim 1 in which the housing is a shape connection.

7. Medical instrument support device comprising:
a harness with a plate that is fixable on the chest of an operator;
a first fastening element orthogonally projecting from the plate;
a second fastening element that is complementarily and removably attached to the first fasting element, said second fasting element rotatable about an axis substantially orthogonal to said plate;
an articulation element having a tubular and elongated shape fixed integrally and removably at a first end to the second fastening element and supporting at a second end a housing angularly adjustable in space, said housing fixable in any angular position around a substantially vertical axis via a clamp, the housing configured to support an associated medical instrument, and wherein said articulation element is flexible so as to allow for deformation into a sinuous shape for positioning of the housing in space.

8. Device according to claim 7, wherein the articulation element includes segments joined to each other so as to form a chain succession and each segment is held in friction contact to the adjacent segments by a tension element so as to maintain a mutual position via friction.

9. Device according to claim 8, wherein a knob is operatively connected to the articulation element and configured such that rotation thereof regulates a friction force between the segments.

10. Device according to claim 9, wherein the second fastening element is snap fastened to the first fastening element thereby exerting pressure or tension respective for extraction or insertion.

11. Device according to claim 9, wherein the second fastening element is fastened to the first fastening element by a gripper which tightens the first fastening element and is operable in a closed or opened position via a lever control in such a way that the second element is rotatable through an azimuth around said axis orthogonal to the plate.

12. Device according to claim 1, wherein the housing is a shape connection.

* * * * *